United States Patent [19]

Hara et al.

[11] Patent Number: 4,563,353

[45] Date of Patent: Jan. 7, 1986

[54] HAIR GROWER FOR ANIMALS

[75] Inventors: Kenji Hara, Ichikai; Eiji Iijima, Utsunomiya, both of Japan

[73] Assignee: KAO Corporation, Tokyo, Japan

[21] Appl. No.: 445,713

[22] Filed: Nov. 30, 1982

[51] Int. Cl.⁴ ............................................. A61K 35/78
[52] U.S. Cl. .................................................. 424/195.1
[58] Field of Search ........................................ 424/195

[56] References Cited

PUBLICATIONS

Chem Abst. Ogawa et al. 88:126179a, Extracts of Coix Lacryma-Jobi 1978.
Steinmetz Codex Vegetabilis, Coix Lacryma Jobi #329 1957.

Primary Examiner—Albert T. Meyers
Assistant Examiner—John W. Rollins
Attorney, Agent, or Firm—Oblon, Fisher, Spivak, McClelland & Maier

[57] ABSTRACT

A hair grower for animals comprising coix seeds or an extract thereof is disclosed. Also disclosed a method for increasing animal's hair in which animals are fed with a feed containing such hair grower.

3 Claims, No Drawings

HAIR GROWER FOR ANIMALS

BACKGROUND OF THE INVENTION (i) Field of the Invention

This invention relates to a hair grower for animals. More particularly, it relates to a hair grower for animals which comprises an effective amount of coix seeds or an extract thereof.

(ii) Description of the Prior Art

Coix seeds (coicis semen) are seeds of pearl barley (Coix Ma-yuen Roman or Coix Lachryma-Jobi L.var. Ma-yuen Stapf) and have long been internally used as a crude drug for the purpose of urination, analgesic and antiphlogistics. The coix seed is now believed to contain an anticarcinogen, coixenolide ($C_{38}H_{70}O_4$) and is taken in admixture with other herb or Chinese medicines so that it serves as a stomachic and ensures urination, good intestines and improvement of appetite. The seed which has been hulled and refined contains about 14% of proteins and is thus utilized as a raw material for rice crackers or other confectioneries in the capacity of seeds which are rich in proteins. Additionally, coix seeds have been privately used for food from old because it is believed to have an effect of removing warts.

SUMMARY OF THE INVENTION

We have made an investigation of the pharmacological action of coix seed or its extract by internal application thereof to animals and unexpectedly found that it serves to promote the growth of animal hair.

That is, the present invention provides a hair grower for animals which comprises coix seeds or their extract as its effective component.

DETAILED DESCRIPTION OF THE INVENTION AND PREFERRED EMBODIMENTS

It is not known as to what component contained in the coix seed or its extract has such an action as mentioned above. The hair grower for animals according to the invention may be admixed with coix seeds themselves or an extract from the seeds. If the coix seed itself is used, it is preferable to use a powder of coix seeds in consideration of its digestibility. In this connection, however, when the hair grower of the invention is added to a feed, coix seeds may be compounded as they are.

The coix seed extract to be used in the practice of the invention, i.e. a substance containing an effective component of coix seed, can be obtained by the following various methods. The extract may be used as it is or after concentration or dilution with or dissolution in water or alcohols.

(i) Raw or dried coix seeds are extracted with water, a hydrophilic organic solvent such as an alcohol, acetone or the like, or a mixed solvent of water and water-soluble organic solvent and the resultant extract is filtered to collect a filtrate. If necessary, the solvent is removed and concentrated.

(ii) The extract or concentrate or the concentration residue is extracted with water and subjected to filtration to remove insoluble matters therefrom thereby collecting a soluble fraction. This fraction may be concentrated, if necessary.

(iii) Coix seeds are infused with alcohols such as ethanol and the resulting infusion is admixed with an insoluble or sparingly soluble fat or oil such as tsubaki oil, castor oil or the like and further with water, followed by agitation and allowing to stand thereby separating into two phases. The alcoholic, aqueous phase is collected.

(iv) The aqueous, alcoholic, or alcoholic aqueous solution obtained in the methods (i)–(iii) and containing the effective component is spray-dried to obtain a powder.

The above extraction may be effected either by a cold infusion or by a hot infusion and is preferably conducted at a temperature of 40°–60° C. for several hours to several days.

The above-described methods of making the extract of coix seed or dried extract are described only by way of an example and extracts obtained by any other methods may be likewise used in the practice of the invention.

The dose of coix seeds or their extract which is an effective component of the hair grower of the invention is in the range of 10 mg–10 g/kg, preferably 100 mg–1.5 g/kg, per day when coix seeds themselves are used. They are internally dosed once or several times a day. On the other hand, when the coix seed extract is used, it is convenient to internally apply it once or several times a day in a total amount of 1–500 mg/kg, preferably 10–100 mg/kg, as solids. However, the amount is not critical and may be arbitrarily changed as required.

The internal administration of the hair grower of the invention is feasible by any known methods and the most convenient method is an admixture of the grower with feeds.

The hair grower of the invention can be applied to almost all of mammals having hair or fur such as, for example, rabbit, cat, dog, mink, sheep, fox, rat, goat and the like.

The present invention is particularly described by way of the following examples.

EXAMPLE 1

To 13 kg of hulled coix seeds was added 130 kg of water for hot infusion (about 40° C.) for 24 hours and the resulting infusion was spray-dried to obtain about 1 kg powder of coix seed extract.

This extract powder was used to give a rat feed having the following composition.

|  | Control Group | Coix Seed Extract Administration Group |
|---|---|---|
| Soybean oil | 100 g | 100 g |
| α-starch | 598 | 597.25 |
| Cellulose | 40 | 40 |
| Vitamins (Harper mixture) | 20 | 20 |
| Minerals (Harper mixture) | 40 | 40 |
| Choline chloride | 2 | 2 |
| Casein | 200 | 200 |
| Coix seed extract powder |  | 0.25 |

| (1) Vitamin | | |
|---|---|---|
| Ingredient | | Proportion |
| Vitamin A-acetate | IU | 46600 |
| Vitamin D | " | 23300 |
| Vitamin E-acetate | mg | 1200 |
| Vitamin $K_1$ | " | 6 |
| Vitamin $B_1$-hydrochloride | " | 59 |
| Vitamin $B_2$ | " | 59 |
| Vitamin $B_6$-hydrochloride | " | 29 |
| Vitamin $B_{12}$ | " | 0.2 |
| Vitamin C | " | 588 |
| D-Biotin | " | 1 |
| Folic Acid | " | 2 |

-continued

| | | |
|---|---|---|
| Calcium Pantothenate | " | 235 |
| Nicotinic Acid | " | 294 |
| Inositol | " | 1176 |
| Lactose | " | Balance |

(2) Mineral

| Ingredient | % |
|---|---|
| CaHPO$_4$.2H$_2$O | 0.43 |
| KH$_2$PO$_4$ | 34.31 |
| NaCl | 25.06 |
| Fe-Citrate | 0.623 |
| MoSO$_4$.7H$_2$O | 9.99 |
| ZnCl$_2$ | 0.02 |
| MnSO$_4$ 6H$_2$O | 0.121 |
| CuSO$_4$.5H$_2$O | 0.156 |
| KI | 0.0005 |
| CaCO$_3$ | 28.28 |
| (NH$_4$)$_6$Mo$_7$O$_{24}$.4H$_2$O | 0.0025 |

The feeds were each given to four weeks-old, male, SD rats for 3 weeks (15–18 g/rat per day). At the 22nd day after commencement of the test, the rats were sheared on their back by means of a hair cutter and an electric razor and were continuously raised using the above feeds to measure a gowth rate of hair. The results are shown below, in which the values indicated are average values of 10 rats.

| | Control Group | Coix seed Extract Administration Group |
|---|---|---|
| 4th day after shearing | 3.89 ± 0.62 mm | 4.66 ± 0.63 mm |
| 7th day after shearing | 7.53 ± 0.41 | 9.06 ± 0.92 |
| 11th day after shearing | 9.41 ± 0.87 | 13.16 ± 1.86 |

It was observed that with the group of administrating the coix extract powder, the growth of the hair was promoted significantly at a level of significance of below 1% at the seventh day and at a level of below 0.1% at the eleventh day as compared with that of the control group.

At the eleventh day after the shearing, the rats were all killed to measure a weight of hair (average of five rats) per unit area of skin, with the result that the weight of the control group was 5.28±1.01 mg/cm$^2$ and the weight of the administration group was 11.32±3.33 mg/cm$^2$, which was about twice as great as that of the control group.

EXAMPLE 2

One gram of the extract powder obtained by the method of Example 1 was sufficiently admixed with 299 g of a concentrate for sheep to give a hair grower for sheep. This grower was fed in an amount of 300 g per day to male Suffork sheep, each weighing about 60 kg, which were bred in groups each consisting of 8 sheep. At the tenth day after commencement of the administration, the sheep were completely sheared at the intercostal thereof with a hair cutter and a razor, followed by continuously raising with the feed and measuring the growth rate of wool. Aside from the above feed, hay, beet grounds and mineral salts were arbitraily fed. The results are shown below, in which each value is an average of 30 specimens of each sheep and, in total, 240 specimens of 8 sheep.

| | Control Group | Coix Seed Extract Powder Administration Group |
|---|---|---|
| 15th day after shearing | 3.72 ± 0.90 mm | 4.27 ± 0.95 mm |
| 20th day after shearing | 4.29 ± 1.00 mm | 5.31 ± 1.34 mm |

It was found that with the coix extract administration group, the growth of hair was promoted in each case at a significance level of below 0.1% as compared with the control group. Moreover, at the twentieth day after the shearing, a given area of the skin of each sheep was sampled to measure a density of wool, with the result that it was 31.4±7.3 mg/cm$^2$ for the control group and 37.5±8.2 mg/cm$^2$ for the coix extract powder administration group.

EXAMPLE 3

13 g of broken pieces of coix seeds was well admixed with 287 g of a concentrate for sheep to give a hair grower for sheep. Sheep were raised under the same conditions as in Example 2 to measure the growth rate of wool. The results are just as shown below.

| | Control Group | Coix Seed Administration Group |
|---|---|---|
| 15th day after shearing | 3.64 ± 0.43 mm | 4.25 ± 0.59 mm |
| 20th day after shearing | 4.31 ± 0.91 mm | 5.29 ± 1.17 mm |

It was found that the administration group showed a significantly promoted rate of hair growth at a significance rate of below 0.1% as compared with the control group.

EXAMPLE 4

60 days old, male C3H mice whose hair on the back was at the second resting stage were sheared so that their back was not damaged and were raised with use of a feed used in Example 1, followed by continuing the raising. The ratio of an area of freshly growing hair to the sheared area and a hair-growing rate were measured. The results are shown below, in which each value is an average of twenty mice.

(1) Hair-growing Rate

| | Control Group | Administration Group |
|---|---|---|
| 3rd day | 0% | 0% |
| 6th day | 0 | 5 |
| 10th day | 10 | 15 |
| 13th day | 30 | 80 |
| 14th day | 40 | 100 |
| 17th day | 100 | |

(2) Ratio of an Area of Freshly Growing Hair to Sheared Area

| | Control Group | Administration Group |
|---|---|---|
| 13th day | 11% | 11% |
| 17th day | 67 | 69 |
| 19th day | 82 | 96 |
| 24th day | 96 | 98 |

With the coix seed extract administration group, the commencement of growth becomes earlier by 3–4 days than that of the control group. Furthermore, the administration group is superior in the area of the freshly growing hair against the sheared area to the control group.

What is claimed is:

1. A method for promoting hair growth in animals having normal hair growth comprising feeding said animals with an effective amount for promoting hair growth of Coix Ma-yuen Roman seeds or an extract thereof obtained by extracting said seeds with water, water-soluble organic solvents or mixed solvents of water and water-soluble organic solvents.

2. The method according to claim 1, further comprising admixing said coix seeds or the extract thereof with a feed for animals having normal hair growth.

3. The method according to claim 1 wherein said amount of coix seeds is in the range of 10 mg to 10 g/kg per day and of said extract is in the range of 1–500 mg/kg as solid.

* * * * *